United States Patent [19]

Lin et al.

[11] Patent Number: 5,582,828
[45] Date of Patent: Dec. 10, 1996

[54] **ACTIVE FRACTIONS OF *CORDYCEPS SINENSIS* AND METHOD OF ISOLATION THEREOF**

[75] Inventors: Ching-Yuang Lin, 4F, No. 193, Sec. 2, Ho-Ping E. Rd., Taipei, Taiwan; Ming-Shi Shiao, Taipei; Zu-Nan Wang, Tainan, both of Taiwan

[73] Assignee: Ching-Yuang Lin, Taipei, Taiwan

[21] Appl. No.: 404,762

[22] Filed: Mar. 15, 1995

[51] Int. Cl.$^6$ .......................... A61K 35/78; A61K 31/56; C12N 1/14

[52] U.S. Cl. .................... 424/195.1; 435/254.1; 514/169

[58] Field of Search ..................... 424/195.1; 435/254.1; 514/169

[56] References Cited

U.S. PATENT DOCUMENTS 4,769,231  9/1988  Ogura et al. .............................. 424/74

*Primary Examiner*—John W. Rollins
*Attorney, Agent, or Firm*—Bacon & Thomas

[57] ABSTRACT

A method for identifying and isolating the active fractions in *Cordyceps sinensis*. It covers a findings of the structure of an active compound that is present in the active fraction, an isolation method that can be used to extract the active fractions and a specific active compound, and the use of "H1-A", one specific active compound that is present in the active fractions thus isolated, to ameliorate the clinical symptoms and renal lesions in laboratory mice with induced IgA nephropathy (Berger's disease). This work has important pharmacological implications for the suppression of activated mesangial cells and IgA nephropathy in humans.

7 Claims, 6 Drawing Sheets

Cordyceps Sinensis (Stroma)
↓  Dry in a dark place at 45-50°C
Net weight
↓  1. Grind finely
↓  2. Methanolic extraction (1:20, W/V)
↓  3. Decompression and concentration
Methanolic extract (CS-M)
↓  Silica gel cartridge column chromatography F1   *F2   F3   F4   F5   F6
↓ Silica gel cartridge column chromatography C1-C10   *C11   C12-C18
↓ Preparative layer chromatography T1   T2   T3   *T4   T5   T6
↓ Reversed-phase high performance liquid chromatography (RP-HPLC)

Spectroscopic information of active marker compound H1-A.

1. Molecular formula: $C_{28}H_{42}O_2$

2. $^1H$-NMR: see Fig 6

3. Mass fragments (EIMS) (m/z): 410 (molecular ion, base peak), 395, 367, 349, 325, 285, 267, 253, 241, 213, 191, 173, 125, 4. $^{13}C$-NMR $(CDCl_3)$ $(\delta)$:
11.95 (q), 17.65 (q), 19.66 (q), 19.97 (q), 21.12 (q), 23.73 (q), 24.59 (t), 24.74 (t), 29.47 (t), 30.69 (t), 33.11 (d), 34.67 (t), 35.57 (t), 40.31 (d), 41.81 (d), 41.89 (t), 42.35 (s), 42.88 (d), 48.43 (d), 53.35 (d), 72.05 (d), 126.81 (d), 132.15 (d), 134.05 (s), 135.49 (d), 160.96 (s), 161.60 (s), 186.65 (s),

ACTIVE FRACTIONS OF *CORDYCEPS SINENSIS* AND METHOD OF ISOLATION THEREOF

BACKGROUND OF THE INVENTION

This invention relates to a method of isolating the fractions of *Cordyceps sinensis* and extracting the constituent H1-A, which can suppress the activated human mesangial cells, alleviate IgA nephropathy (Berger's disease), and prevent the disease from progressing to the uremia stage.

Recent studies have demonstrated the multiple pharmacological actions of *Cordyceps sinensis* (Clavicipitaceae), which is a fungus that develops stroma and is found on the larvae of the lepidoptera caterpillar. The pharmacological actions include:

1. Immune System

In animals, the extracts of *Cordyceps sinensis* raise the phagocytic index of macrophage and stimulates the secretion of interleukin 1; it induces proliferation of splenic Thy-1 cells and stimulates the synthesis and secretion of IgM. It also stimulates the replication of T lymphocytes and increases the number of interleukin 2 receptors expressed on B lymphocytes. The aqueous extract increases the activity of natural killer cells in both normal subjects and leukemia patients.

2. Renal Function

*Cordyceps sinensis* reduces damages to renal tubules and protects the $Na^+$, $K^+$-ATPase on cellular membranes, an action which is associated with a reduction in cellular lipid perioxidation. It can decrease chronic renal insufficiency. In rats, it can alleviate hematuria and reduce the elevation of serum creatinine.

3. Cardiovascular System

An extract of *Cordyceps sinensis* increases the volume of blood flow in the coronary arteries of experimental animals. It also reduces resistance and pressure in arteries, brain, and peripheral vascular system. Adenosine, the main water-soluble constituent, acts to relax vascular smooth muscle and causes vasodilatation. *Cordyceps sinensis* also promotes platelet formation, helps prevent hypoxia, and acts as a monoamine oxiduse (MAO) inhibitor.

No purified compounds from *Cordyceps sinensis* have been used before to evaluate the above-mentioned pharmacological actions. None of the researches conducted on alleviating the histological symptoms of renal pathology were based on any animal model of IgA nephropathy.

Clinically, IgA nephropathy presents as paroxysmal hematuria and/or proteinuria, and it always runs a chronic course. The disease gradually progresses to uremia in 20% of adult patients in Taiwan. To date, no therapeutic agent has been shown to stop its progression. Hence there is a pressing need for development of a curative substance. The pathogenesis of IgA nephropathy is as follows:

Mesangial deposition of nephritogenic IgA immune complexes in glomeruli activates the resting mesangial cells. The activated mesangial cells start to release cytokines including interleukin 1 (IL-1), interleukin 6 (IL-6), and tumor necrosis factor α (TNF α). These cytokines cause mesangial cells to release growth factors such as platelet-derived growth factor (PDGF) and transforming growth factor-β (TGF-β) in addition to IL-1 and IL-6. The actions of these cytokines and growth factors are similar to that of autocrine system in which it induces a vicious cycle of mesangial proliferation with release of chemical mediators such as platelet activating factor (PAF), prostaglandin $E_2$ (PGE$_2$), thromboxane $B_2$ (TXB$_2$), neutral proteinase, and free radicals including superoxide union which all lead to the glomerular injury and sclerosis.

Clinically, IgA nephropathy generally presents as paroxysmal hematuria (microscopic or macroscopic) and/or proteinuria. This chronic disease typically runs an asymptotic course interspersed with periodic acute exacerbation. According to previous studies, it progresses to renal failure in 20 to 30% of cases in Spain and France; hence it can be inferred that each year 1 to 2% of the patients diagnosed with IgA nephropathy will progress to renal failure. Unfortunately, no treatment has been shown to arrest the progress of the condition. The etiology of IgA nephropathy is still unknown. However, the extensive deposition of both IgA and complement 3 (C3) on the mesangial area found in renal biopsy shows that the renal damage is probably caused by mesangial deposition of IgA immune complexes in association with activated alternative complement pathway. In brief, nephritogenic IgA immune complexes activate the resting mesangial cells to release cytokines such as interleukins 1 and 6 as well as tumor necrosis factor α (TNF α), causing mesangial cell proliferation accompanied by the release of growth factors including platelet-derived growth factor (PDGF) and transforming growth factor-β (TGF-β). Like autocrine, these cytokines and growth factors not only provoke a vicious cycle of mesangial cell proliferation, but also cause the mesangial cells to release free radicals such as superoxide anion ($O_2^-$) and $H_2O_2$, and chemical mediators such as platelet activating factor (PAF), prostaglandins, thromboxane $B_2$, and neutral proteinase, thereby inducing matrix accumulation, glomerular injury, and sclerosis.

It can be inferred from the above that the treatment of choice would ideally be based on preventing the formation of IgA immune complexes. However technological limitations in the field of immunology preclude these options. Hence attempt was made to settle for a second approach: using specialized isolation techniques, and the inventor started to work out a way to obtain natural products to extract bioactive agents that can suppress activated mesangial cells, thereby preventing their proliferation and the release of cytokines and growth factors. Once the activated mesangial cells have been effectively suppressed and their proliferation arrested, the process that leads to production of cytokines and growth factors can be brought to a halt. Hence the inventor selected in vitro suppression of activated mesangial cells as the screening method in the search for therapeutic agents.

SUMMARY OF THE INVENTION

The main object of the invention is to find certain fractions and compound produced by *Cordyceps sinensis* that can be used to inhibit the proliferation of human mesangial cells and ameliorate the histopathological changes, namely hematuria and proteinuria, in animal models of IgA nephropathy.

To reach the above-mentioned objectives, a method for culturine human mesangial cells in vitro is adopted for investigating the releases of cytokines and chemical substances by activated human mesangial cells and damage of the glomerular basement membrane. Animal models are used for the investigation of IgA nephropathy to find particular fractions and active compounds that may be used in the treatment of the disease.

Other objects and the features of this invention can be understood by reading the following paragraphs of the detailed description and accompanying tables and figures.

Table 1-1 shows the in vitro inhibition on activated human mesangial cells by F-2 fraction from the methanolic extract of *Cordyceps sinensis*.

Table 1-2 shows the in vitro inhibition on activated human mesangial cells by C-11 fraction from the methanolic extract of *Cordyceps sinensis*.

Table 1-3 shows the in vitro inhibition on activated human mesangial cells by T-4 fraction from the methanolic extract of *Cordyceps sinensis*.

Table 1-4 shows the in vitro inhibition on activated human mesangial cells by H1-A fraction from the methanolic extract of *Cordyceps sinensis*.

Table 1-5 shows the in vitro inhibition on activated human mesangial cells by H1-A and lovastatin from the methanolic extract of *Cordyceps sinensis*.

Table 2 shows the results of acute toxicity tests in mice with IgA nephropathy that were fed with a normal diet containing 1% F-2.

Table 3-1 shows the histopathological improvement of IgA nephropathy in mice fed with a normal diet containing F-2.

Table 3-2 shows the histological improvement of IgA nephropathy as illustrated by reduction of deposition of IgA immune complexes in mice fed with a normal diet containing F-2.

Table 3-3 shows the reduction of renal immunofluorescence study on mice with IgA nephropathy that were fed with a normal diet containing F-2.

Table 3-4 shows the reduction of severity of hematuria and/or proteinuria in urine analysis for mice with IgA nephropathy that were fed with a normal diet containing F-2.

This invention involves two main areas of investigation:

A: Isolating the specific fractions F-2, C-11, T-4 and the compound H1-A.

B: Methods and processes to extract the above-mentioned fractions and the compound H1-A.

The above active fractions and active compounds can be used for suppression of the proliferation of human mesangial cells, and the future clinical application of them to reduce the histopathological changes of IgA nephropathy and the concomitant hematuria and proteinuria.

In terms of activation of mesangial cells, [$^3$H]-thymidine incorporation method is used as an index of DNA synthesis. Cultured human mesangial cells are first activated by exposing them to IL-1 and IL-6. The decrease in [$^3$H]-thymidine incorporation after exposure to various fractions and compounds in *Cordyceps sinensis* was used as the in vitro screening method for identifying potential substances which are capable of inhibiting the proliferation of activated human mesangial cells.

An In-Vivo Screening System

The requirements for animal models include both specificity and the capacity for developing renal histopathological lesions that are similar to those found in the corresponding human disorders. In view of the above considerations, the IgA nephropathy models developed by Rifai A. et al were adopted for the experiments used in developing this invention. The selected antigen was R36A, a purified C-polysaccharide obtained from the cell wall of *Streptococcus pneumoniae*, and the antibody employed was the IgA monoclonal antibody that is specific to R36A to form nephritogenic IgA immune complex, which can induce hematuria and proteinuria in mice with IgA deposition in mesangial area. For this experiment, the R36A antigens were i.p injected into mice and the IgA monoclonal antibody (monoclonal antibody specific for R36A) was injected into the tail vein. The IgA immune complexes formed in the blood vessels of the mice were then transported by the circulating system to the kidney, where they became deposited in the mesangial area leading to henmturia and protcinuria. Subsequent renal biopsy on these mice, and renal tissue stained by Hematoxyline-Eosin stain, revealed histopathological changes similar to those found in human IgA nephropathy, i.e. proliferation of mesangial cells and mesangial deposition. Further application of fluorescent staining techniques to frozen biopsy specimens also revealed mesangial depositions of IgA and C3 similar to those found in human IgA nephropathy.

Toxicity

In ICR mice the $LD_{50}$ of *Cordyceps sinensis* was 21.7±2.6 g/kg for injection into the abdominal cavity, and 24.5±2.2 g/kg for injection into the tail vein. In terms of oral administration, the maximal tolerance dose was 252.5–300 g/kg, a result which shows that irrespective of whether dosage is achieved by means of injection into the abdominal cavity or tail or by gastric implantation, this substance has a very low level of toxicity. The methodology used to carry out acute toxicity testing for this invention was as follows: ICR mice that had been fed on a normal diet with the above active compound included to constitute a 2% ratio were killed after 5 days in order to ascertain whether there was any evidence of toxicity.

These results show that *Cordyceps sinensis* has a broad range of pharmacology actions and low toxicity. Previous study has established that IgA nephropathy is a form of nephritis without currently known medicinal substance that can be used to treat it. For these reasons, I undertook research to identify the effective active fractions and active compounds in *Cordyceps sinensis* that could both suppress proliferation of activated mesangial cells in vitro and prevent the occurrence or exacerbation of IgA nephropathy in vivo. Two screening methods were adopted for the purposes of this study: suppressing the proliferation of activated cultured human mesangial cells; and amelioration of the symptoms of induced IgA nephropathy in vivo, using mice as the study models. This work was undertaken in the hope that substances thus identified could be used in the treatment of IgA nephropathy.

Figure 2:
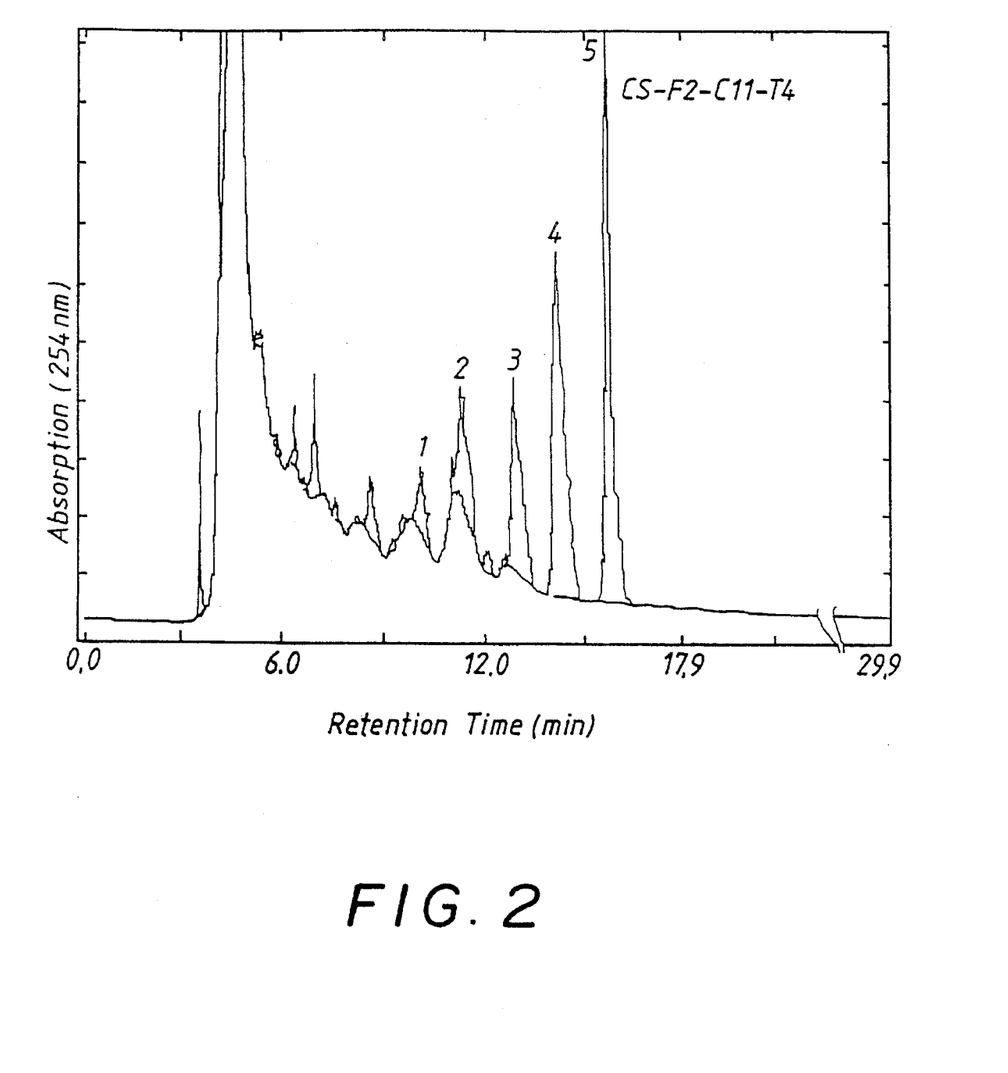
FIG. 2 shows reversed-phase liquid chromatogram of this invention's fraction T-4 (serial number CS-F2-C11-T4).

The methods used to obtain these active fractions and the compound H1-A are detailed below:

item one:

As shown in FIG. 2, this invention provides a method for obtaining fractions and a compound H1-A from the fungus of *Cordyceps sinensis*. First, the sample is either air dried or in an oven (35°–60° C.). *Cordyceps sinensis* has a very high moisture content in its crude form, so drying is necessary to minimize the amount of polar substances that are drawn out in the extraction process, as these would affect the results of silica gel column chromatographic purification. Next, the dried product is ground in a grinder or miller to increase the efficiency of extraction.

Figure 1:
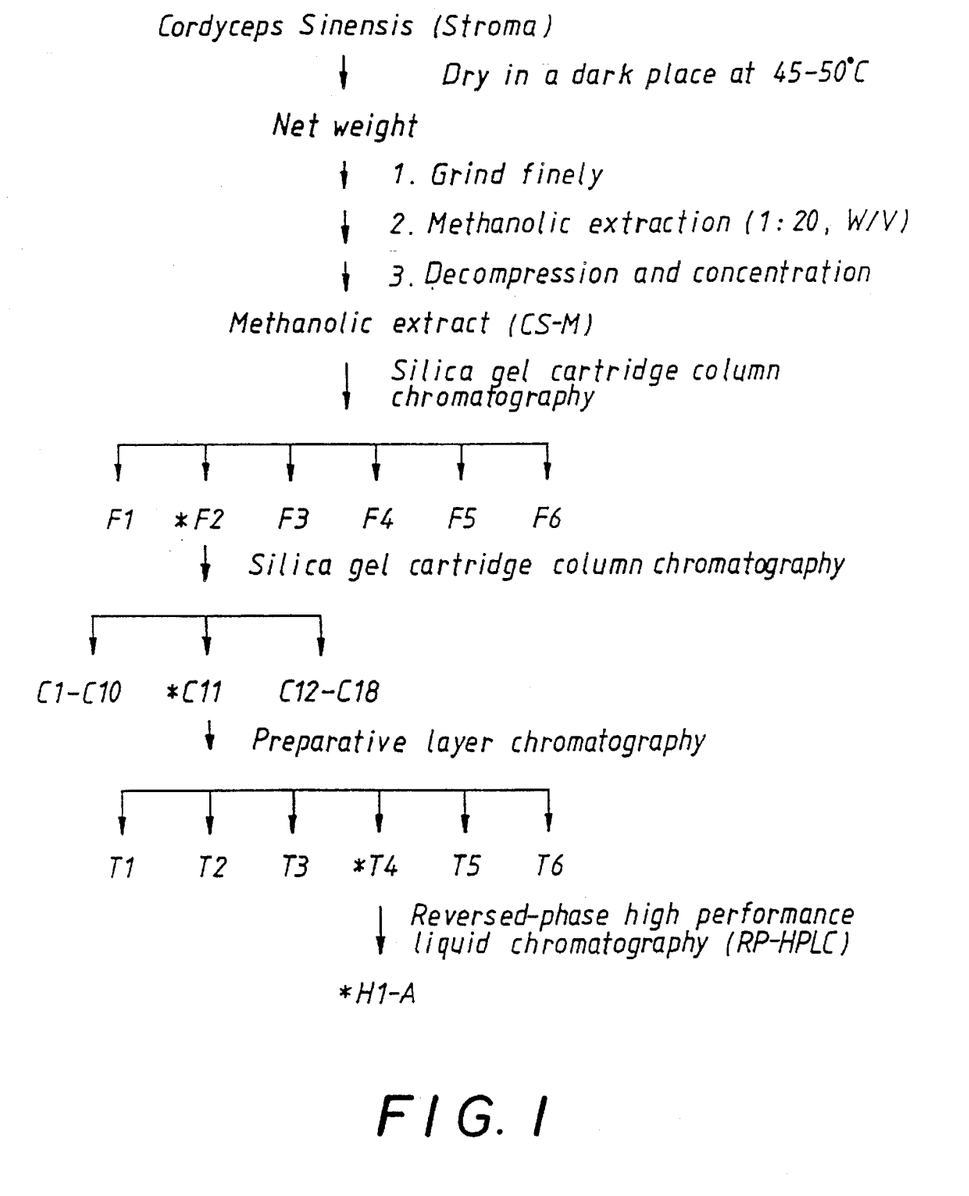
FIG. 1 shows a process used in this invention to extract the specific fractions and compounds H1-A from the stroma of *Cordyceps sinensis*.

The polarity range of the active compounds in *Cordyceps sinensis* (in terms of suppressing the activated mesangial cells and improving renal function as described herein) is relatively low, so these substances can be effectively extracted by using methanol (or other low-carbon alcohol), acetone, diethyl ether, ethyl acetate, chloroform, or methylene chloride. However considering the advantages of containing a high return of desired fractions and compound H1-A with minimal extraction of polar contaminants, methanol and ethyl acetate are the most suitable choice. Methanol extraction was used as an extraction and the procedure is depicted in FIG. 1.

Figure 3A:
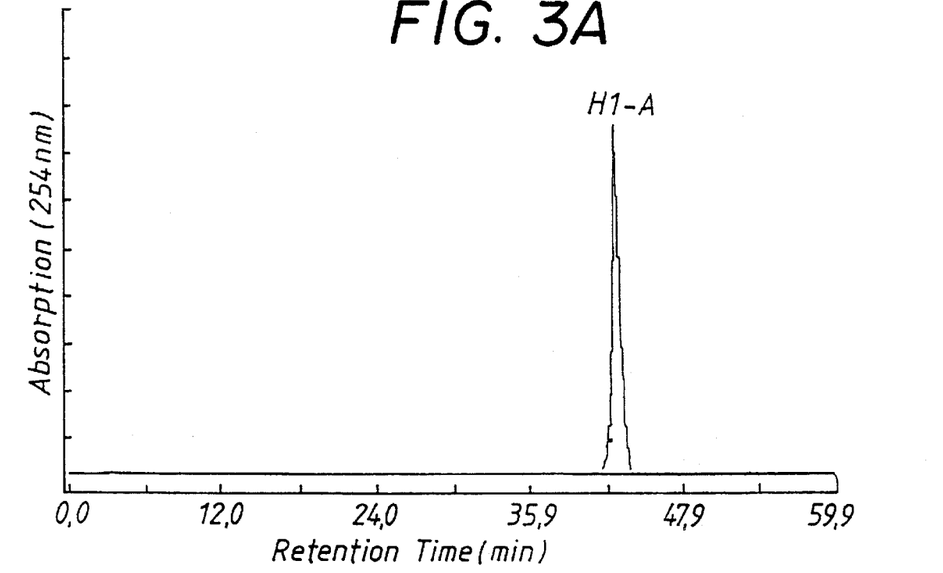
FIG. 3 shows reversed-phase liquid chromatogram for compound H1-A, the completely purified compound in this invention.
Figure 3B:
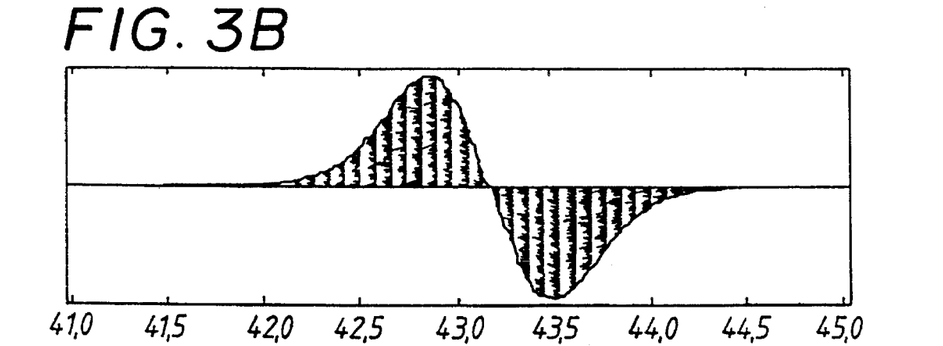
Figure 3C:
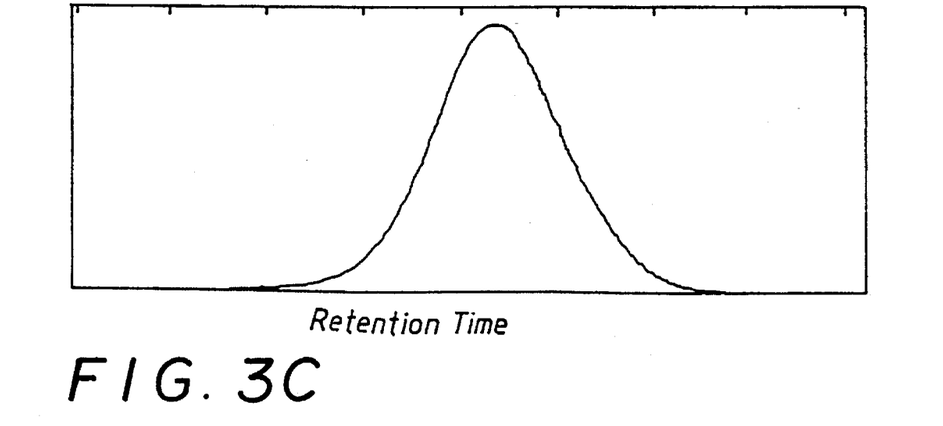

The chromatographic methods used are depicted in FIG. 2 and 3. The methods used were based on the amount of substance being analyzed, as follows:

A: A method to ascertain the biological activity and quantity of compounds H1-A present in a small amount of *Cordyceps sinensis*.

B: A method to progress the specific fractions (F-2, C-11 and T-4) and compound H1-A from larger amounts of *Cordyceps sinensis*, using an activity index to monitor the chromatographic process.

In Respect of Item A: (Chromatographic Analysis of Small Samples)

A small amount of the methanolic extract from *Cordyceps sinensis* is passed through a reversed-phase cartridge column and subsequent elation is carried out by using methanol. The above-mentioned fractions and compound are not retained during this process but many contaminants of very low polarity are adsorbed and removed. The screening test can be carried out on the eluate. Quantitative determination (for chromatographic requirements, see actual results) of H1-A can be conducted by using reversed-phase high performance liquid chromatography (KP-HPLC). Initial screening of the concentrates can also be carried out.

If ethyl acetate is chosen as the solvent for the extraction, then after the extract has been concentrated to a suitable extent it can be added to an equivalent amount of n-hexane (or petroleum ether). The resultant mixture is filtered through glass wool before being passed through a silica gel cartridge column. The cartridge column should be continuously eluted with ethyl acetate/n-hexane (1:1, v/v). RP-HPLC or activity test as mentioned above can then be carried out on the elute after it has been concentrated.

In Respect of Item B: (Chromatographic Analysis of Relatively Large Samples)

Because the insect larvae is the host, *Cordyceps sinensis* samples contain vast amounts of lipophilic metabolites, which interfere greatly with the extraction and isolation processes. Hence silica gel column chromatography is carried out in two stages: the first stage is designed to separate the specific fraction (F-2) from the large number of contaminating substances which are lower in polarity than the active compounds. Generally speaking, these contaminants are flushed out using n-hexane combined with a small percentage of ethyl acetate (for example n-hexane with ethyl acetate in a ratio of 4:1, v/v). Subsequently, the polarity of the mobile phase is increased so that the fraction, which contains H1-A and other active compounds, is eluted. The procedures remove both high and low polarity contaminants, thereby greatly increasing the activity index of the fractions so that it can be put directly to use in experimental animals. At the same time, the amount of material that remains for the second cycle of silica-gel chromatography is greatly reduced. In view of the nature of the constituents found in *Cordyceps sinensis*, the first stage silica-gel chromatography greatly reduces the interference matter. The second stage chromatography completely separates out the desired fractions which contain compounds. Namely, the second stage is not simply a repetition of the first. For extract of cultured mycelia, only the second stage separation is sufficient, as there are far less low-polarity contaminants in cultured mycelia than in prepared stroma.

The actual implementation of this invention is detailed below:

The stroma of *Cordyceps sinensis* is dried in a dark place at a temperature of 45°–50° C. After grinding, it is soaked in methanol at a ratio of 1:20 (w/v) for 24 hours. After the resulting crude extract has been concentrated, separation of silica gel cartridge-column chromatographic is carried out to collect fractions by being eluted with n-hexane/ethyl acetate (1:1, v/v) to neat ethyl acetate. When separating larger amounts of sample, finer separation of the methanol extract (or F-2 fraction) can be achieved by means of elation with an n-hexane-ethyl acetate mixture utilizing incremental addition of ethyl acetate. The solvent ratio is 1:2 (v/v) for the portion obtained by elation (C-11). The F-2 and C-11 fractions show the strongest biological activities in terms of suppressing activation of human mesangial cells. These two active fractions can be stored at 4° C. for at least 3 months without losing any of the effects mentioned above.

To extract the compounds H1-A from the fraction, preparative-layer silica gel chromatography (silica gel PLC) can be carried out on C-11 to eliminate more contaminants. Using n-hexane/ethyl acetate (1:1, v/v) as developing solvent the plate is developed twice. The Rf range for recovery is 0.5 to 0.7 (T-4 zone). This process is similar to silica gel cartridge-column chromatography in terms of its isolation mechanism, but it can further remove C-11 layer contaminants with resultant advantages later when semi-preparative RP-HPLC is used to purify the T-4 layer. In this process, methanol is used as the eluate for the reversed-phase liquid chromatographic process. The stationary phase of the semi-preparative column utilizes the reversed phase C18 (8×250-mm, 5-μm) mode, and the flow rate is 2 ml/min. The UV detector should be set at the wavelength of 254 nm. By using the above procedures, the key compound H1-A can be obtained in its pure form.

For a summary of the process used to obtain both the specific fractions and compound H1-A in pure form, please refer to supplementary FIG. 1. For reversed-phase liquid chromatogram of both the fraction T-4 and the pure form of H1-A, please see supplementary FIG. 2 and 3.

The methods for culturine mycelia and containing their presence are outlined below:

Culture of a strain of *Cordyceps sinensis* (VGH-CS-1) in a liquid medium containing the following constituents:

| | |
|---|---|
| Glucose | 2% |
| Peptone | 0.5% |
| Malt extract | 2% |
| Potato-dextrose broth | 24 g/l |

Figure 4:
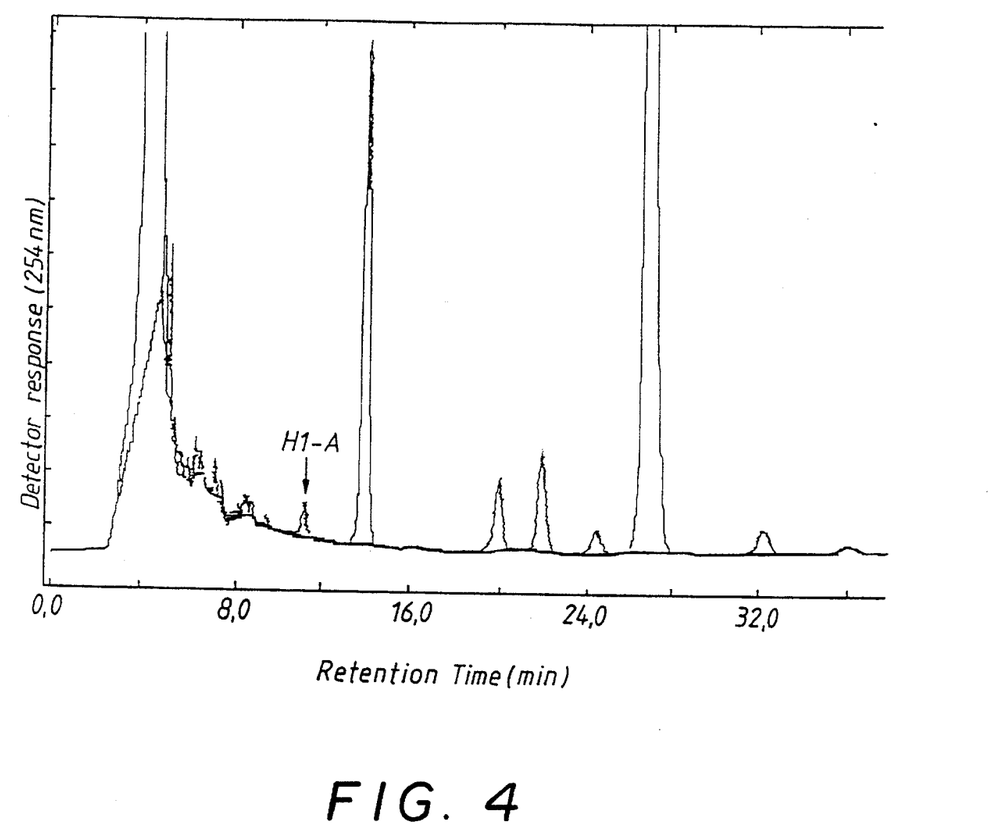
FIG. 4 shows reversed-phase liquid chromatogram for a methanol extract from cultured mycelia of *Cordyceps sinensis* as obtained through the application of this invention.

Leave to culture at 26±1.0° C. for 30 days, then collect the mycelia and dry at 45 to 50° C. Grind the resulting mycelial products and place them in methanol at a ratio of 1:20 (dry weight/volume) for an extraction period of 24 hours. Concentrate (VGH-CS-1-MX) the resulting crude extract. Carry out reversed-phase high performance liquid chromatographic analysis oil VGH-CS-1-MX to ensure it contains the active compound H1-A (see supplementary FIG. 4).

In summary, item 1 covers both the liquid cultured and semi-cultivated *Cordyceps sinensis* in a liquid-phase medium, and the methods for assaying the above-mentioned fractions and compound H1-A.

Item Two: Specific Fractions and Compound H1-A

A: Specific Fractions: This term refers to those fractions that are obtained during the entire isolation process and in each chromatographic cycle, from methanol extraction to final purification of compound H1-A, and demonstrate the strongest activity in vitro. These include fractions F-2, C-11 and T-4.

Figure 5:
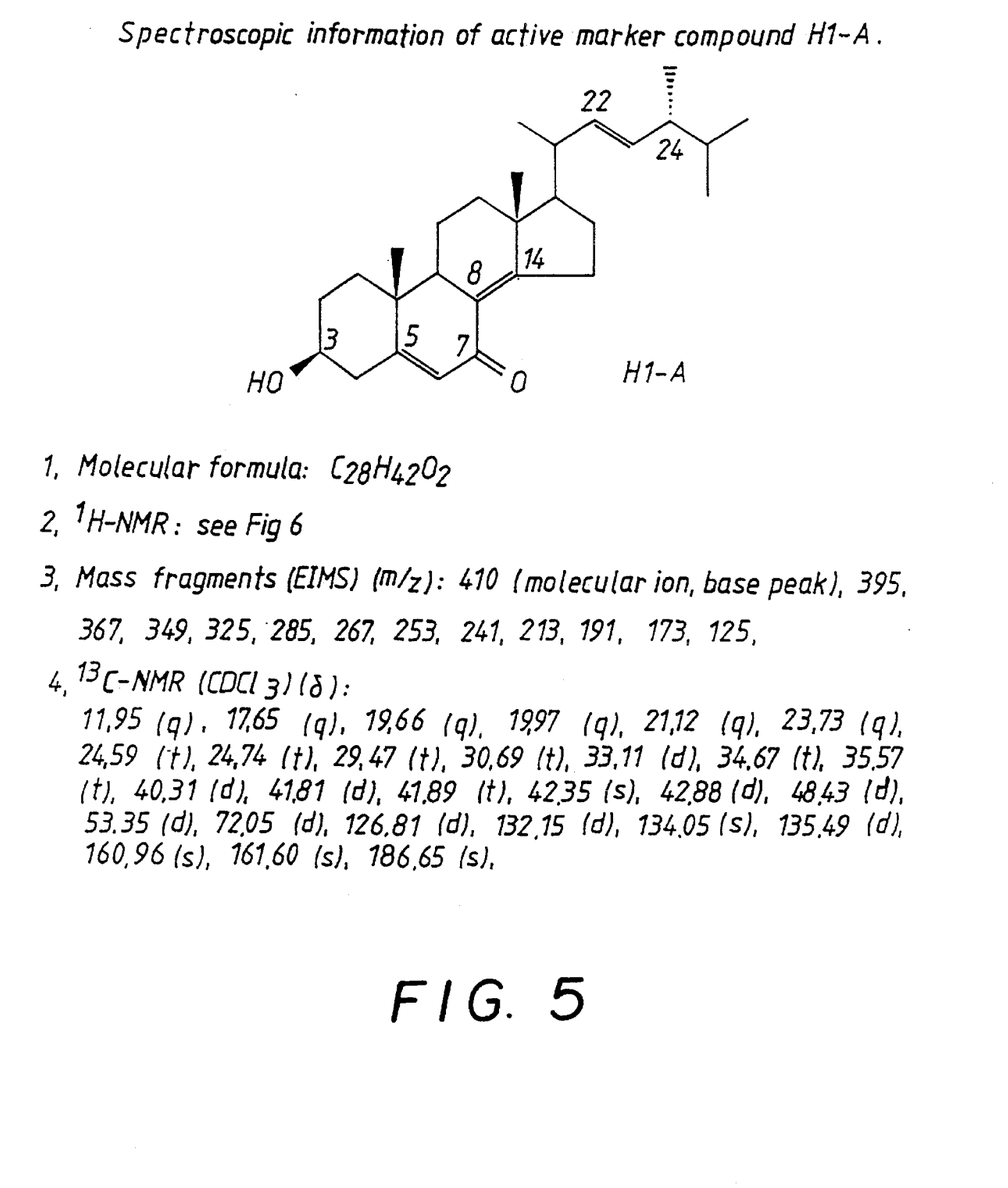
FIG. 5 shows the structure of compound H1-A of this invention.
Figure 6:
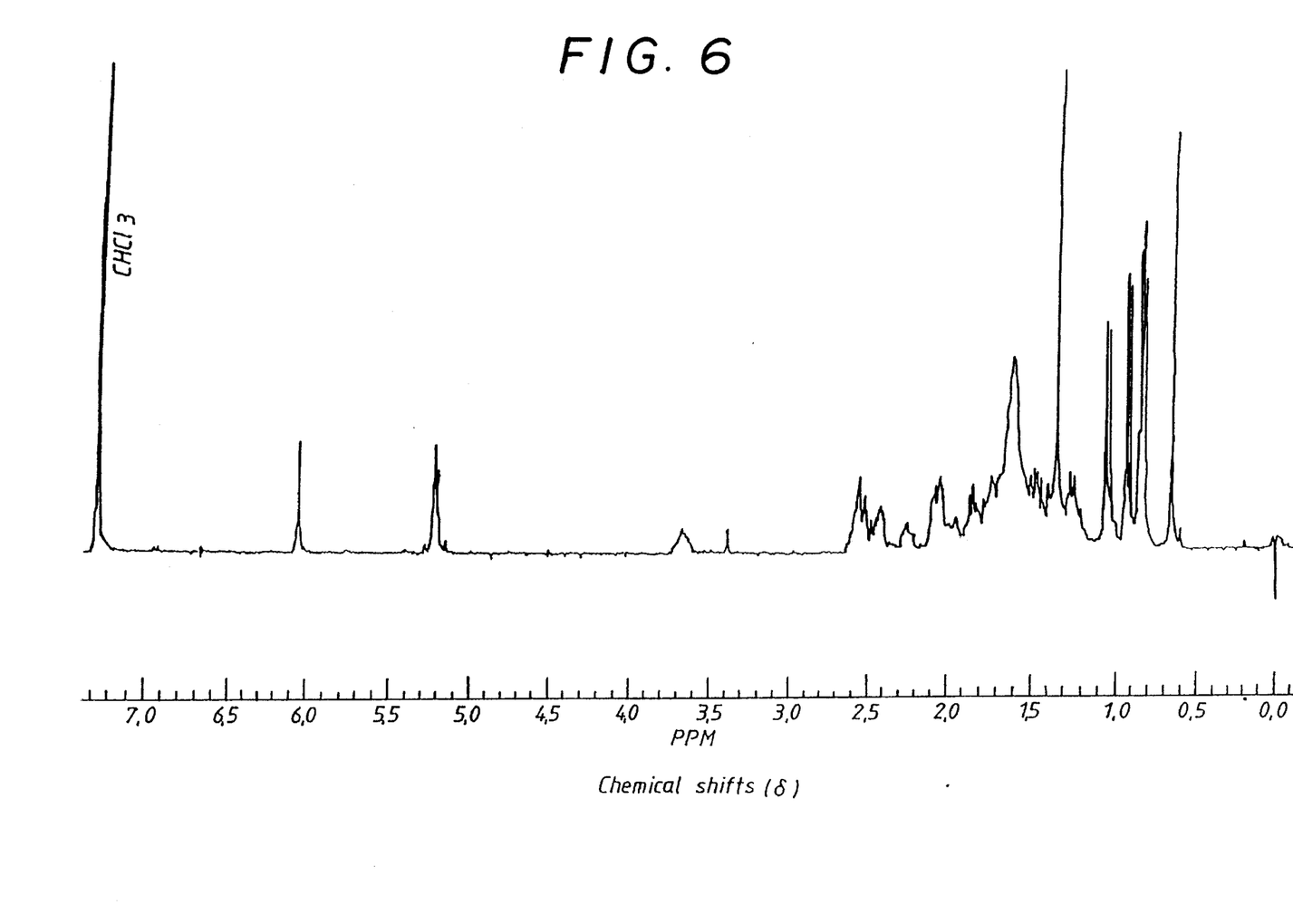
FIG. 6 shows the proton nuclear magnetic resonance ($^1$H-NMR) spectrum of H1-A.

B: Compound H1-A: This refers to H1-A (for spectroscopic and structural data, see FIGS. 5 and 6). To confirm the potential applicability of the above fractions and to check for obvious toxicity or mutagenicity, Ames test and acute toxicity test were conducted on ICR mice, using the F-2 fraction. The results showed no obvious evidence of toxicity or mutagenic properties.

Item Three

Two methods of investigation (in vitro and in vivo) were adopted for the invention discussed in the patent application. One of these utilizes in vitro suppression of activated human mesangial cells as its model: the activity index used is the degree to which activation by interleukins 1 and 6 is suppressed by treatment with the fractions and purified compound H1-A of *Cordyceps sinensis*. Isotope-labeled [$^3$H]-thymidine converted into [$^3$H]-thymidine incorporation is the basis by which the degree of activation of mesangial cells is determined (please see Tables 1-1 to 1-5).

Item Four: Acute Toxicity Test

Experimental animals were divided into two groups (each consisting of six animals). One group was fed on a diet containing 2% CS-F2, and the other on the same diet without this additive, The mice were killed after 5 days. Table 2 shows that in the control group, induction of IgA nephropathy with nephritogenic IgA immune complexes caused hepatomegaly (the average liver weight/100 g body weight ratio was 7.12±0.12). On a diet containing 2% F-2, there was marked amelioration of the hepatomegaly (the average liver weight/body weight ratio was 6.75±0.09). As for liver function, both groups were within the normal range (see Table 2).

Item Five: Pharmacological Effect In Vivo

The animals (Balb/o mice) were given antigen (R36A) via intraperitoneal injection, while monoclonal antibody (anti-R36A-IgA mAb) was injected into tail veins. The procedure induced the symptoms of IgA nephropathy. The animals developed hematuria and proteinuria, and pathological investigation showed IgA and C3 deposition in the pathological mesangial area. The active fractions of *Cordyceps sinensis* (such as F-2) were combined with the animals' feed at ratios of 0.5% and 1%, in order to evaluate their effectiveness in ameliorating the above-described symptoms and pathological manifestations (please see supplementary Table 3-1 to 3-4). The results clearly confirm the effectiveness of the active fraction of *Cordyceps sinensis* in ameliorating experimentally induced IgA nephropathy.

In summary, F-2, a fraction isolated from *Cordyceps sinensis* by using this invention can suppress the proliferation of activated mesangial cells in vitro and bring to a halt the ensuing progression of renal damage. In vivo, it can prevent exacerbation of IgA nephropathy and ameliorate hematuria and uremia. Furthermore F2 not only does not cause acute toxicity, but it can even bring about amelioration of hematomegaly provoked by IgA immune complexes. The $GI_{50}$ (growth inhibition50) of HI-A, the natural substance obtained through purification of F2, is calculated (for 50% inhibition of proliferation) at 40 µM. From this, it can be calculated that approximately 40 mg if H1-A would be effective in the treatment of IgA nephropathy in humans. It should be appreciated that the disclosure described above is new and useful.

TABLE 1-1

The in vitro inhibitory action on activated human mesangial cells of the F-2 fraction from the methanolic extract of *Cordyceps Sinensis*.

|  |  | 0 | 50 mcg/ml | 100 mcg/ml |
|---|---|---|---|---|
| F-2 | (n = 3) | 0 | 51.0 ± 6.3%* | 94.0 ± 11.3% |
| Control group | (n = 3) | 0 | 0 | 0 |

*% of inhibition
Control group: the active fraction *Cordyceps Sinensis* was not utilized.

TABLE 1-2

The in vitro inhibitory action on activated human mesangial cells of the C-11 fraction from the methanolic extract of *Cordyceps Sinensis*.

|  |  | 0 | 50 mcg/ml | 100 mcg/ml |
|---|---|---|---|---|
| C-11 | (n = 3) | 0 | 88.4 ± 11.6%* | 90.4 ± 11.8% |
| F-2 | (n = 3) | 0 | 23.9 ± 2.3% | 84.4 ± 10.5% |
| Control group | (n = 3) | 0 | 0 | 0 |

*% of inhibition
Control group: the active fraction *Cordyceps Sinensis* was not utilized.

TABLE 1-3

The in vitro inhibitory action on activated human mesangial cells of the T-4 fraction from the methanolic extract of *Cordyceps Sinensis*.

|  |  | 0 | 50 mcg/ml | 100 mcg/ml |
|---|---|---|---|---|
| C-11 | (n = 3) | 0 | 69.0 ± 9.7%* | 98.0 ± 10.5% |
| T-4 | (n = 3) | 0 | 85.0 ± 5.0% | 98.0 ± 0.7% |
| Control group | (n = 3) | 0 | 0 | 0 |

*% of inhibition
Control group: the active fraction *Cordyceps Sinensis* was not utilized.

TABLE 1-4

The in vitro inhibitory action on activated human mesangial cells of the H1-A fraction from the methanolic extract of *Cordyceps Sinensis*.

|  |  | 0 | 10 mcg/ml | 20 mcg/ml | 40 mcg/ml | 50 mcg/ml |
|---|---|---|---|---|---|---|
| T-4 | (n = 3) | 0 | 42.2 ± 9.9%* | 66.3 ± 18.5% | 71.5 ± 2.5% | 97.9 ± 3.5% |
| H1-A | (n = 3) | 0 | 23.0 ± 9.6% | 51.2 ± 11.9% | 66.3 ± 6.8% | 82.7 ± 11.5% |
| Control group | (n = 3) | 0 | 0 | 0 | 0 | 0 |

*% of inhibition
Control group: the active fraction *Cordyceps Sinensis* was not utilized.

TABLE 1-5

The in vitro inhibitory action on activated human mesangial cells by lovastatin and
H1-A from the methanolic extract of *Cordyceps Sinensis*.

|  |  | 20 μM | 50 μM | 75 μM | 100 μM |
|---|---|---|---|---|---|
| H1-A | (n = 3) | 30.8 ± 4.9% | 61.6 ± 7.5% | 69.5 ± 5.6% | 83.2 ± 3.5% |
| Lovastatin | (n = 3) | 19.8 ± 2.0% | 37.1 ± 4.3% | 60.9 ± 3.8% | 73.0 ± 4.0% |
| Control group | (n = 3) | 0 | 0 | 0 | 0 |

TABLE 2

Results of acute toxicity testing in mice with IgA nephropathy
that were fed on a normal diet with 1% F-2 content.

|  | Control group (6 animals) | 1% F-2 (6 animals) |
|---|---|---|
| Liver weight (g.) | 1.03 ± 0.03 | 1.00 ± 0.04 |
| Body weight (g.) | 14.5 ± 0.34 | 14.8 ± 0.40 |
| Liver weight/body weight ratio (100 g./g.) | 7.12 ± 0.12 | 6.75 ± 0.09 |
| Liver function |  |  |
| ALT (units/liter) | 83.3 ± 10.3 | 77.5 ± 3.59 |
| AST (units/liter) | 315 ± 36.9 | 346 ± 24.2 |
| Cholesterol (mg/liter) | 1.76 ± 0.18 | 1.46 ± 0.02 |

TABLE 3-1

The histopathological effects of a normal diet with 0.5% and 1% F-2 content on mice
with IgA nepthropathy.

|  |  | No. 1 | No. 2 | No. 3 | No. 4 | No. 5 | No. 6 | Total |
|---|---|---|---|---|---|---|---|---|
| 1% F-2 | (n = 6) | 2+ | 2+ | 2+ | 2+ | 2+ | 2+ | 12+* |
| 0.5% F-2 | (n = 6) | 4+ | 4+ | 4+ | 3+ | 4+ | 3+ | 22+ |
| Control group | (n = 6) | 4+ | 4+ | 4+ | 4+ | 4+ | 4+ | 24+ |

Grading: 0, 1+, 2+, 3+, 4+ (5 grades; count 50 glomeruli)
H & E stain: 1% F-2 v.s. control group: $P < 0.05$
The group fed on a diet with 1% F-2 content exhibited significant improvement in terms of
histopathological observations

TABLE 3-2

The immunopathological effects of a normal diet with 0.5% and 1% F-2 content on
mice with IgA nephropathy.

|  |  | Deposition of IgA immune complexes | | | | | | |
|---|---|---|---|---|---|---|---|---|
|  |  | No. 1 | No. 2 | No. 3 | No. 4 | No. 5 | No. 6 | Total |
| 1% F-2 | (n = 6) | 0 | 1+ | 1+ | 0 | 1+ | 1+ | 4+* |
| 0.5% F-2 | (n = 6) | 1+ | 1+ | 1+ | 1+ | 1+ | 1+ | 6+ |
| Control group | (n = 6) | 2+ | 2+ | 2+ | 2+ | 2+ | 1+ | 11+ |

Grading: 0, 1+, 2+, 3+ (4 grades)
1% F-2 v.s. control group: $P < 0.05$
The group fed on a diet containing 1% F-2 exhibited significant decreases in the amount of IgA
immune-complex deposition.

TABLE 3-3

The results of renal immunofluorescence studies on mice with IgA nephropathy that were fed on a normal diet containing 0.5% and 1% F-2.

| | | Deposition of complement 3 | | | | | | |
|---|---|---|---|---|---|---|---|---|
| | | No. 1 | No. 2 | No. 3 | No. 4 | No. 5 | No. 6 | Total |
| 1% F-2 | (n = 6) | 1+ | 0 | 1+ | 0 | 1+ | 0 | 3+* |
| 0.5% F-2 | (n = 6) | 2+ | 1+ | 2+ | 0 | 3+ | 1+ | 9+ |
| Control group | (n = 6) | 2+ | 2+ | 2+ | 2+ | 3+ | 3+ | 14+ |

Grading: 0, 1+, 2+, 3+ (4 grades)
1% F-2 v.s. control group: P <0.05
The group fed on a diet with 1% F-2 content exhibited significant decreases in the amount of complement 3 deposition.

TABLE 3-4

The results of urine analysis for mice with IgA nephropathy that were fed on a normal diet containing 0.5% and 1% F-2.

| | Hematuria and/or proteinuria (>+/3+) | | |
|---|---|---|---|
| | Control group (n = 6) | 0.5% F-2 (n = 6) | 1% F-2 (n = 6) |
| Day 5 | 2/6 (33.3%) | 2/6 (33.3%) | 2/6 (33.3%) |
| Day 6 | 2/6 (33.3%) | 2/6 (33.3%) | 2/6 (33.3%) |
| Day 7 | 3/6 (50.0%) | 1/6 (16.6%) | 1/6 (16.6%)* |

*P <0.05
By day 7, the groups fed on a diet containing 0.5% and 1% F-2 exhibited significant decreases in hematuria and proteinuria.

We claim:

1. Active fractions of *Cordyceps sinensis* obtained by a method comprising the steps of:
   (a) drying stroma portions of *Cordyceps sinensis* in a dark place at 45 to 50 degrees C.;
   (b) grinding the dried stroma portions;
   (c) soaking the ground stroma portions in methanol at a 1:20 ratio (w/v) for 24 hours to produce a crude extract;
   (d) concentrating the crude extract;
   (e) obtaining an F-2 fraction from the crude extract by means of silica gel cartridge column chromatography by eluting with an n-hexane/ethyl acetate mixture at a 1:1 ratio (v/v) to the extractable portion of neat ethyl acetate;
   (g) obtaining a C-11 fraction from the F-2 fraction by mean of silica gel cartridge column chromatography by eluting with an n-hexane/ethyl acetate mixture utilizing incremental addition of ethyl acetate at a collection ratio of 1:2 (v/v), wherein the F-2 and C-11 fractions exhibit biological activity in terms of suppressing activation of human mesangial cells, and can be stored at 4 degrees C. for at least 3 months without loss of biological activity.

2. An active compound obtained from the active fractions of *Cordyceps sinensis* obtained in claim 1 by a method comprising the steps of:
   (a) obtaining a T4 fraction from the C-11 fraction by means of silica gel preparative layer chromatography by developing the C-11 fraction twice by eluting with n-hexane/ethyl acetate (1:1 v/v) as developing solvent, wherein the Rf range for recovery is 0.5 to 0.7 (T-4 zone); and
   (b) carrying out reverse phase high performance liquid chromatography on the T4 fraction to obtain the active compound H1-A in substantially pure form.

3. The active compound according to claim 2, wherein the $GI_{50}$ (growth inhibition50) of H1-A for mice is about 40 M, and the therapeutic dose for treating IgA nephropathy in humans is about 40 mg.

4. Active fractions of *Cordyceps sinensis* obtained by the process of:
   (a) implanting the CS-1 strain of *Cordyceps sinensis* in a liquid-phase culture medium containing the following constituents:

| Glucose | 2% |
|---|---|
| Peptone | 0.5% |
| Malt extract | 2% |
| Potato-dextrose broth | 24 g/l |

(b) culturing the implanted medium at 26±1.0 degrees C. for about 30 days;
   (c) collecting the mycelia and drying the mycelia at 45 to 50 degrees C.;
   (d) grinding the product of step (c) and placing it in methanol at a ratio of 1:20 (dry weight/volume) for an extraction period of 24 hours to form a crude extract;
   (e) concentrating the resulting crude extract; and
   (f) carrying out reversed-phase high performance liquid chromatographic analysis on the crude extract to obtain the active compound H1-A.

5. An active fraction of *Cordyceps sinensis*, in substantially pure form, comprising the active compound H1-A having the molecular formula $C_{28}H_{42}O_2$, and the following structure:

6. A method for obtaining active fractions of *Cordyceps sinensis* comprising the steps of:
   (a) drying stroma portions of *Cordyceps sinensis* in a dark place at 45 to 50 degrees C.;
   (b) grinding the dried stroma portions;
   (c) soaking the ground stroma portions in methanol at a 1:20 ratio (w/v) for 24 hours to produce a crude extract;
   (d) concentrating the crude extract;

(e) obtaining an F-2 fraction from the crude extract by means of silica gel cartridge column chromatography by eluting with an n-hexane/ethyl acetate mixture at a 1:1 ratio (v/v) to the extractable portion of neat ethyl acetate (F-2 fraction);

(g) obtaining a C-11 fraction from the F-2 fraction by means of silica gel cartridge column chromatography by eluting with an n-hexane/ethyl acetate mixture utilizing incremental addition of ethyl acetate at a collection ratio of 1:2 (v/v) to collect the C-11 fraction, wherein the F-2 and C-11 fractions exhibit biological activity in terms of suppressing activation of human mesangial cells, and active fractions can be stored at 4 degrees C. for at least 3 months without loss of biological activity.

7. A method for obtaining an active compound from active fractions of *Cordyceps sinensis* according to claim 6 comprising the steps of:

(a) obtaining a T4 fraction from the C-11 fraction by means of silica gel preparative layer chromatography by developing the C-11 fraction twice by eluting with n-hexane/ethyl acetate (1:1 v/v) as developing solvent, wherein the Rf range for recovery is 0.5 to 0.7 (T-4 zone); and (b) carrying out reverse phase high performance liquid chromatography on the T4 fraction to obtain the active compound H1-A in substantially pure form.

\* \* \* \* \*